(12) United States Patent
Funaoka et al.

(10) Patent No.: US 6,690,024 B1
(45) Date of Patent: Feb. 10, 2004

(54) LASER INSPECTION APPARATUS

(75) Inventors: Koji Funaoka, Tokyo (JP); Masahiko Sakamoto, Tokyo (JP); Shozui Takeno, Tokyo (JP); Hiroshi Sasai, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/618,721

(22) Filed: Jul. 18, 2000

(30) Foreign Application Priority Data

Jul. 21, 1999 (JP) .......................................... 11-205973

(51) Int. Cl.[7] .............................................. G01N 21/88
(52) U.S. Cl. ........................... 250/559.45; 250/559.36; 356/237.4
(58) Field of Search ....................... 250/559.45, 559.35, 250/559.36; 356/614, 635, 237.4, 237.5, 73, 317, 318, 445, 446

(56) References Cited

U.S. PATENT DOCUMENTS

| | | | | |
|---|---|---|---|---|
| 4,639,604 A | * | 1/1987 | Murakami et al. | 250/548 |
| 4,744,663 A | * | 5/1988 | Hamashima et al. | 356/73 |
| 5,216,479 A | * | 6/1993 | Dotan et al. | 356/73 |
| 6,069,689 A | * | 5/2000 | Zeng et al. | 356/73 |

FOREIGN PATENT DOCUMENTS

| | | | |
|---|---|---|---|
| JP | 7-209187 A | 8/1995 | |
| JP | 9-123034 | 5/1997 | ............ B23Q/1/25 |
| JP | 11-108864 | 4/1999 | |
| KR | 1999/36747 | 5/1999 | |

* cited by examiner

Primary Examiner—Edward J. Glick
Assistant Examiner—Chih Kao
(74) Attorney, Agent, or Firm—Sughrue Mion, PLLC

(57) ABSTRACT

A laser inspection apparatus has a light source 13 for outputting laser beam, application means 5, 33, 34 for irradiating the laser beam 7 output from the light source 13 to any desired position of a detected body 21, first detection means 2 for detecting fluorescence 8 generated from the detected body 21 to which the laser beam 7 is applied, and second detection means 3 for detecting reflected light 8 scattered on a surface of the detected body 21 to which the laser beam 7 is applied.

12 Claims, 12 Drawing Sheets

FLUORESCENCE INTENSITY COMPARISON

| NO. OF SHOTS | MERCURY LAMP (RELATED ART EXAMPLE) | 30 - mW LASER |
|---|---|---|
| 3 (DEFECTIVE PIECE AFTER DESMEAR) | 280 | 10 |
| 7 (GOOD PIECE AFTER DESMEAR) | 370 | 104 |

SECTIONAL VIEW OF HOLE

COMPOSITE SIGNAL

DISCRETIZATION DATA

SORT RESULT

CENTER POSITION DETECTION

AVERAGE VALUE OF x1' TO xi' IS ASSUMED TO BE HOLE CENTER POSITION WHERE (MAXIMUM VALUE OF x1' TO xi' - MINIMUM VALUE) < HOLE DIAMETER

DISTRIBUTIONS OF RESIDUAL RESIN

| NO. OF SHOTS | 3 PULSES | 5 PULSES | 7 PULSES |
|---|---|---|---|
| CROSS SECTION OF HOLE | 18, 24 (cross-section) | (cross-section) | (cross-section) |
| AFTER DESMEAR | DEFECTIVE PIECE | GOOD AND DEFECTIVE PARTS ARE MIXED | GOOD PIECE |

LASER INSPECTION APPARATUS

BACKGROUND OF THE INVENTION

1. Field of the Invention

This invention relates to a laser inspection apparatus, for example, having an inspection function of detection, thickness measurement, etc., of an unremoved material left on the bottom face of a blind via hole during blind via hole machining in a multilayer wiring board called a printed wiring board.

2. Description of the Related Art

Making denser wiring has been demanded with recent high performance of the electronic machines. To meet the demand, multilayering and miniaturization of printed wiring boards are advanced. In one of the arts, it is indispensable to make a fine blind hole for interlayer conduction connection having a hole diameter of about 150 µm, called a blind via hole (SVH). However, it is difficult to drill a hole of φ0.2 mm or less and machine a blind hole by the current drilling technique and in addition, an insulating layer of a high-density printed wiring board is 100 µm or less thick and it is difficult to control the depth with the accuracy, thus it is impossible to make a fine BVH by drilling.

Attention is focused on a method of irradiating a laser beam as a BVH making method replacing the drilling. The method uses the light energy absorption difference between a resin or glass fiber of an insulating material forming a part of a printed wiring board and copper of a conductor layer. Carbon dioxide laser is put to some use as a light source of laser beam. As shown in FIG. 11, if inner layer copper foil 24 is previously deposited on the inside of the machined part, dissolving and removal of an insulating member are stopped on the inner layer copper foil 24, so that a blind hole 6 stopped reliably on the inner layer copper foil 24 can be made. Such a machined hole is particularly called a direct image hole. As shown in FIG. 12, on a board comprising copper foil 24a on a surface, a copper foil removal part of a necessary hole diameter is formed by etching, etc., and laser beam 20 having a beam diameter larger than the hole diameter of the removal part is applied, whereby a machined hole 6 can also be made. Such a machined hole is particularly called a conformal image hole.

If the blind hole stopped on the copper foil is machined by carbon dioxide laser as shown in FIGS. 11 and 12, the resin of the insulating member 1 µm or less thick is left on the inner layer copper foil if a sufficient laser beam is applied. Thus, after laser machining, it is necessary to etch the residual resin in a permanganic acid, etc., for completely removing the residual resin. At this time, if the blind hole is lessened to about 100 µin diameter, the etching liquid becomes hard to spread all over the inside of the hole, thus if the residual resin becomes thick exceeding a thickness of 1 µm because of a failure of the laser machining condition, etc., a hole where the residual resin cannot completely be removed occurs. In this state, if plating is applied and a BVH electrode is formed, the resin remains left in a part between the plate film and the inner layer copper foil. Here, if a stress is exerted by a heat cycle, etc., with it as the start point, the plate film peels off. Thus, it becomes necessary to inspect the thickness of the remaining resin after laser machining.

FIG. 13 a residual resin distribution when the number of shots is changed. It is known that the residual resin is a little observed in the vicinity of the center of a hole and is easily left in the vicinity of the wall faces of the hole. Like a hole made with the number of shots, five pulses, the resin is a little observed at the center position, but is much in the surroundings as a defective piece. Therefore, to inspect the residual resin for thickness, it is necessary to inspect a wide range from the center to the periphery.

An inspection apparatus in a related art uses an optical microscope to inspect a machined part as shown in FIG. 14. If a resin is left about 10 µm or more thick, it can be detected under the optical microscope in the related art described on page 45 of Nikkei Science October 1990 issue, but the optical microscope is poor in detection accuracy of the residual resin about several µm thick as described above and is hard to apply in mass production. The post-plated machined part must be cut and ground, then the residual resin must be inspected for thickness by observing the cross section; the inspection takes time and 100% inspection cannot be conducted; this is a problem.

The reason why the residual resin cannot be detected under the optical microscope in the related art is as follows:

The optical microscope in the related art has a configuration as shown in FIG. 15. Illumination white light 38 is applied through an object lens 5 to a printed wiring board 21 by a beam splitter 25. Reflected light from the printed wiring board 21 forms an inverted real image 27 enlarged by the object lens 5 forward of an image formation lens 9, and the real image is detected by a CCD camera 11.

As shown in FIG. 16, when the while light 38 of illumination light of the optical microscope is applied to the surface of residual resin 22, some is reflected and other light passes through the residual resin 22 and reaches copper foil 24 on the bottom and is reflected thereon. Therefore, if the white light 38 is applied to thin resin on the copper foil as illumination light, most reflected light is returned from the copper foil 24 and thus the residual resin 22 becomes invisible.

FIG. 17 shows an inspection apparatus described as one embodiment in JP-A-7-83841. In the figure, numeral 43 denotes an ultraviolet laser light source, numeral 45 denotes a collimation lens, numeral 44 denotes a mirror, numeral 25 denotes a beam splitter, numeral 46 denotes a rotary polyhedral mirror, numeral 21 denotes a printed wiring board to be inspected, numeral 9 denotes an image reformation lens, numeral 48 denotes a pin hole, and numeral 47 denotes a photomultiplier (photomultiplier tube).

Next, the operation of the related art example is as follows: Laser beam generated by the ultraviolet laser beam source 43 is enlarged using the collimation lens 45. The enlarged laser beam is scanned using the rotary polyhedral mirror 46 and is condensed on the printed wiring board 21 through the object lens 5.

The ultraviolet light generated from the printed wiring board 21 by irradiating the laser beam reversely traces the incident path, is fed back recursively, and is guided into a recursive reflection sense system by the beam splitter 25 placed in the optical path. The ultraviolet reflected light is formed through the image formation lens 9. An image in the proximity of the application point of the laser beam to the printed wiring board to be inspected is observed on the image formation face. Only the center portion is separated through the pin hole 48 placed in the image formation face and is detected by the photomultiplier 47.

Since the inspection apparatus in the related art shown in FIGS. 15 and 16 is configured as described above, if the residual resin is thin, the reflected light is strong and the residual resin cannot be detected as described above; this is a problem.

The inspection apparatus shown in FIG. 17 executes laser scanning on the rotary polyhedral mirror. The laser beam scan line may shift from the center line of the blind hole because of a position shift at the blind hole machining time, worsening of precision of the scanner, etc. For example, if the residual resin is a little observed in the vicinity of the hole center at a good level, but the periphery is at a defective level like the blind hole made with the number of shots, five pulses, a good piece may be erroneously determined a defective piece because of a scan line shift; this is a problem.

To prevent this, it is necessary to make the scan line spacing sufficiently smaller than the hole diameter and scan the full hole bottom face, but it takes enormous time in inspection; this is a problem.

To inspect a conformal board, since copper foil exists on the board surface, if laser beam is applied to any other portion than a blind hole, fluorescence is not generated, thus a defective piece is erroneously determined a good piece; this is a problem.

SUMMARY OF THE INVENTION

It is therefore an object of the invention to provide an inspection apparatus capable of inspecting a recess reliably and at high speed.

According to one aspect of the invention, there is provided a laser inspection apparatus comprising a light source for outputting laser beam, application means for irradiating the laser beam from the light source to any desired position of a detected body, first detection means for detecting fluorescence generated from the detected body to which the laser beam is applied, and second detection means for detecting reflected light scattered on a surface of the detected body to which the laser beam is applied.

According to another aspect of the invention, there is provided a laser inspection apparatus comprising a light source for outputting laser beam, application means for irradiating the laser beam from the light source to any desired position on a board formed with a recess, detection means for detecting fluorescence generated from the board to which the laser beam is applied and outputting a detection signal, and control means for controlling the application means based on the detection signal, characterized in that the application means scans laser beam in a predetermined direction in the proximity of the recess, the detection means detects strength change of the fluorescence generated from the board as the laser beam is scanned, and outputs a detection signal, and the control means calculates a tentative center position of the recess on the scan line based on the detection signal, then the application means is controlled by the control means so as to scan laser beam in a direction passing through the calculated tentative center position and orthogonal to the scan line.

The control means discretizes the detection signal and sorts the discretized data in the level order of the detection signal and further makes a comparison with the diameter of the recess previously stored, thereby calculating the tentative center position of the recess.

According to still another aspect of the invention, there is provided a laser inspection apparatus comprising a light source for outputting laser light, application means for irradiating the laser beam from the light source to any desired position on a board formed with a recess, first detection means for detecting fluorescence generated from the board to which the laser beam is applied and outputting a first detection a signal, second detection means for detecting reflected light scattered on a surface of the board to which the laser beam is applied and outputting a second detection signal, and control means for controlling the application means based on the first and second detection signals, characterized in that the application means scans laser beam in a predetermined direction in the proximity of the recess, the first detection means detects strength change of the fluorescence generated from the board as the laser beam is scanned, and outputs a first detection signal, the second detection means detects strength change of the reflected light scattered on the board as the laser beam is scanned, and outputs a second detection signal, and the control means calculates a tentative center position of the recess on the scan line based on the first and second detection signals, then the application means is controlled by the control means so as to scan laser beam in a direction passing through the calculated tentative center position and orthogonal to the scan line.

The control means discretizes the first detection signal and sorts the discretizes data in the level order of the first detection signal and further makes a comparison with the diameter of the recess previously stored, thereby calculating the tentative center position of the recess.

The control means discretizes the second detection signal and sorts the discretizes data in the level order of the second detection signal and further makes a comparison with the diameter of the recess previously stored, thereby calculating the tentative center position of the recess.

The second detection means is placed so that the angle from the board face is set equal to or less than the aspect ratio of the recess.

The second detection means is placed like a ring.

The control means combines the first and second detection signals.

The control means discretizes a composite signal provided by combining the first and second detection signals and sorts the discretized data in the level order of the composite signal and further makes a comparison with the diameter of the recess previously stored, thereby calculating the tentative center position of the recess.

The application means executes scanning in the same direction two times or more.

The laser inspection apparatus further includes position detection means for detecting an actual scan position at the laser scanning time.

DETAILED DESCRIPTION OF THE PRESENT INVENTION

First Embodiment

Figures 1, 2:
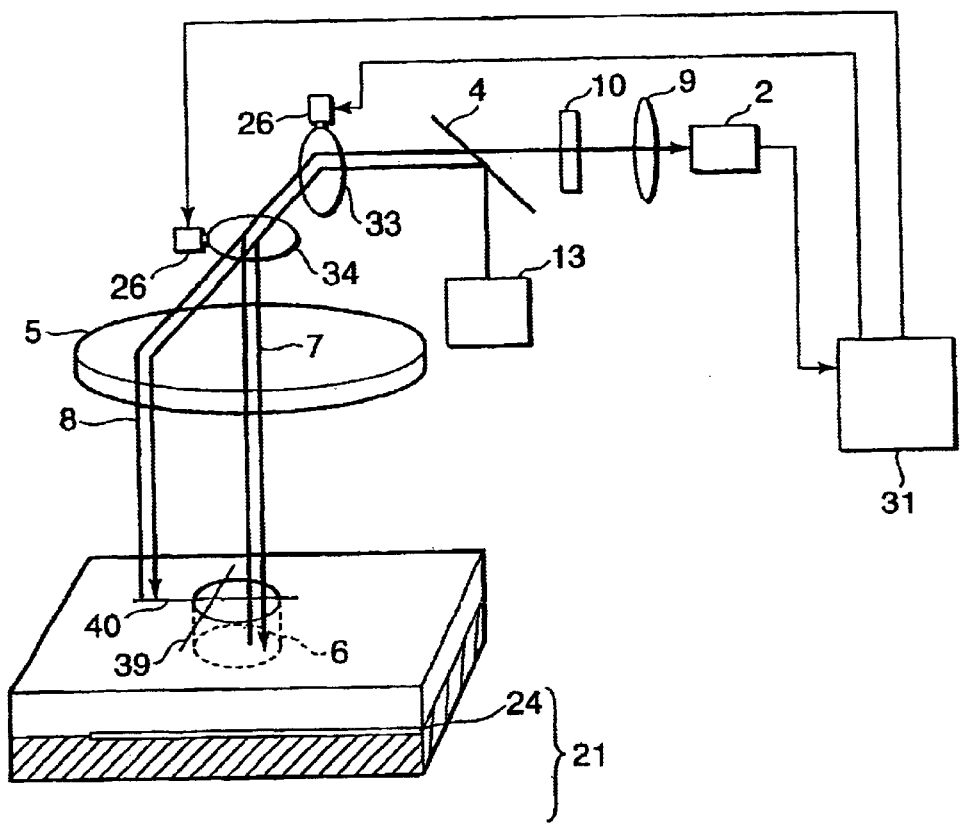
FIG. 1 is a drawing to show the configuration of a laser inspection apparatus of a first embodiment of the invention.
FIG. 2 is a drawing to show fluorescence intensity comparison.

FIG. 1 is a drawing to show the configuration of a laser inspection apparatus of a first embodiment of the invention. In the figure, numeral 13 denotes a laser, numeral 4 denotes a dichroic mirror for reflecting laser beam output from the laser 13, numerals 33 and 34 denote galvanomirrors for scanning laser light in X and Y directions respectively, numeral 5 denotes an object lens for condensing the scanned laser beam onto a printed wiring board 21, numeral 10 denotes a filter for selecting a wavelength of fluorescence generated from the printed wiring board 21 to which laser beam is applied and passing through the dichroic mirror 4, numeral 9 denotes an image formation lens for transferring the fluorescence, and numeral 2 denotes a detector for detecting the fluorescence. A central processing room 31 gives a scan position command to a galvanometer 26 and drives it. A signal of the fluorescence detector 2 is input to the central processing room 31 for making a determination.

Next, the operation of the laser inspection apparatus of the invention shown in FIG. 1 is as follows: As in the related art example, when laser beam is applied to a resin part or a resin remaining part of a blind hole, fluorescence is generated. The fluorescence has a wavelength longer than laser beam has (generally, visible light). The dichroic mirror 4 is adapted to reflect the laser beam output from the laser 13 and allow light of any other wavelength to pass through. The filter 10 is used to select only the wavelength to be inspected as light entering the detector 2.

In the embodiment, the laser 13 uses a 30-mW solid laser of wavelength 473 nm. Hitherto, to observe fluorescence, ultraviolet light generally has been used because the fluorescence intensity can be observed higher by using ultraviolet light if the power is the same. However, since the ultraviolet light is largely absorbed and lost unless a special optical system of silica glass, etc., is used and since the optical system is expensive, laser beam having the wavelength 473 nm is used. A mirror for reflecting wavelengths of 495 nm or less is used as the dichroic mirror 4, and the filter 10 does not allow wavelengths of 520 nm or less to pass through. A carbon dioxide gas laser is used to machine a blind hole in a printed wiring board.

The number of shots of carbon dioxide gas laser is changed and the light strength of fluorescence generated by a printed wiring board using mercury lamp is compared with that using 30-mW solid laser beam and the result is shown in FIG. 2 (since the exposure time (seconds) is described in FIG. 2, the light strength becomes the reciprocal of the numeric value). The printed wiring board is machined with the number of shots, seven pulses and then desmear treatment is conducted, whereby the residue of resin is not observed.

If the residue of resin on the bottom part of a blind hole in a printed wiring board is about 0.2 $\mu$m to 0.6 $\mu$m, it is shown that the residue of resin can be removed by executing desmear treatment of a laser step. According to FIG. 2, it is seen that to use the mercury lamp, the light strength of fluorescence generated scarcely changes between defective and good pieces, but if the solid laser beam is used, the fluorescence intensity difference between the defective and good pieces is about 10 times.

As described in [Related arts], if carbon dioxide gas laser machining is normally complete, the resin remainder less than 1 $\mu$m thick occurs in the bottom part of a blind hole. Thus, with an out-of-phase lamp, etc., light passes through an extremely thin resin, fluorescence is not generated, and an inspection cannot be made. In addition, the strength of fluorescence itself is too strong as a whole, thus it is hard to make a determination.

On the other hand, laser beam in phase with monochromatism is absorbed even in an extremely thin resin of the order of wavelength and fluorescence is generated, so that it is made possible to make an inspection. Therefore, the residue of resin about 0.6 $\mu$m thick on the hole bottom can be removed after desmear treatment and thus is not defective, but if the residue of resin is thicker than about 0.6 $\mu$m, it cannot be removed by desmear treatment. Thus, it turned out that it is effective to use the above-mentioned laser beam to detect a machining failure before desmear treatment after carbon dioxide gas laser machining. In our experiment, since laser beam having the wavelength 473 nm was used, the residue of resin substantially 0.5 $\mu$m or more thick can be detected sufficiently.

In the configuration of the laser inspection apparatus of the invention, the two galvanomirrors are used to make up a scan optical system, thus a move is made to a blind hole from the beginning and an inspection can be made only on the periphery of the blind hole, so that the inspection can be performed at high speed. In contrast, for example, with the observation apparatus in the related art described in JP-A-7-83841, the scan method with the rotary polyhedral mirror is disclosed; since full scanning must be executed over a printed wiring board with fine scan line spacing, it takes very much time.

In the embodiment, the position of a blind hole in the printed wiring board 21 is previously registered in the central processing room 32.

Figure 3:
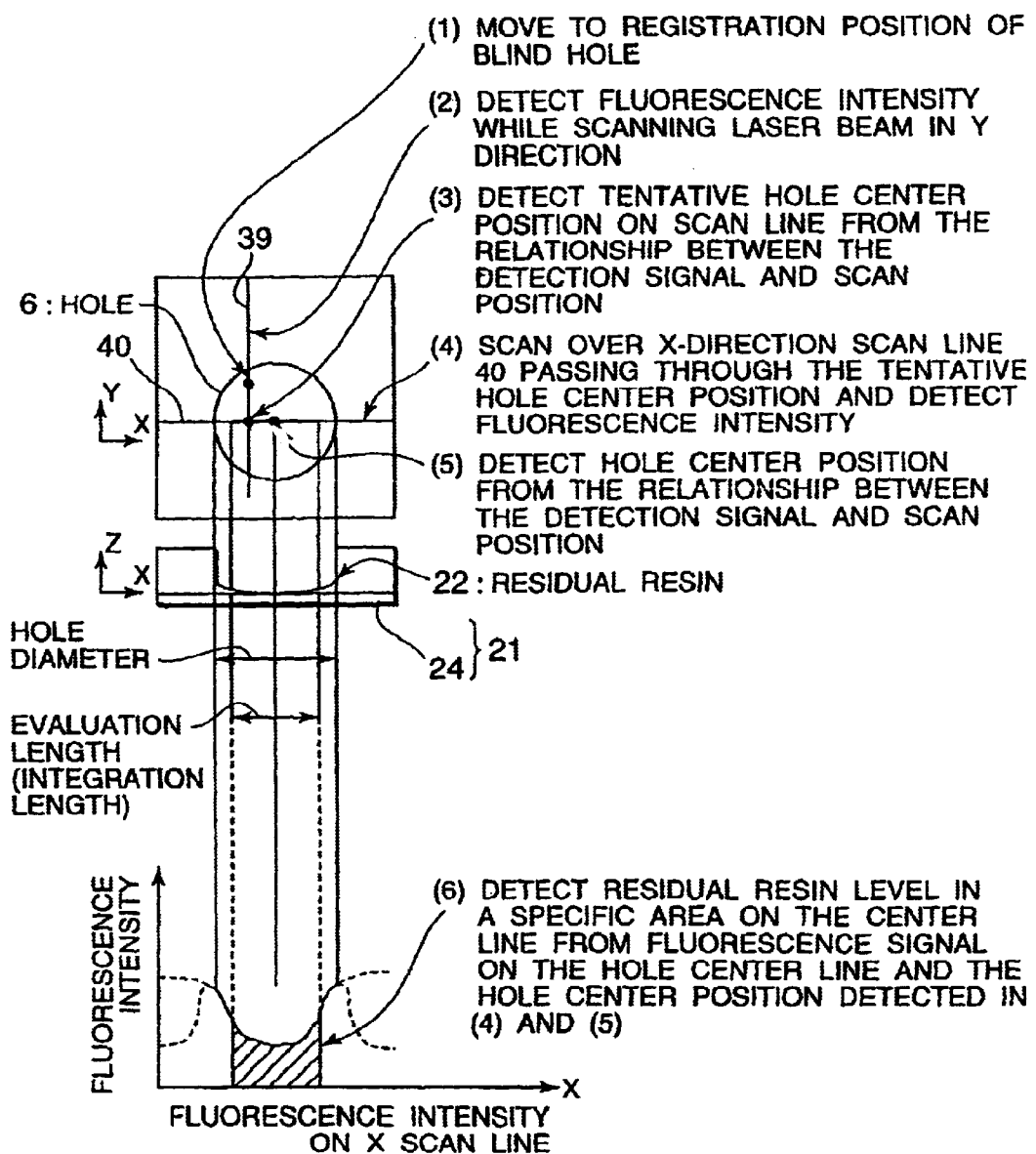
FIG. 3 is a drawing to describe an inspection procedure of remaining resin.

Considering a position shaft of the blind hole at the machining time thereof and the precision of a scanner, if a move is made to the registered blind hole position, a shift may occur between the laser application position and the center position of the blind hole. FIG. 3 is a drawing to describe a scan method for detecting the shift and precisely irradiating the laser beam to the blind hole. After a move is made to the registered blind hole position (1), first, laser scanning is executed over a Y-direction scan line 39 having a length twice as large as the hole diameter with the registered blind hole position as the center (2), and a tentative hole center position is detected from a signal detected by the fluorescence detector 2 (4). Since the true hole center position exists on an X-direction line passing through the tentative hole center position and orthogonal to the Y-direction scan line 39, if laser scanning is executed over X scan line 40, a fluorescence signal on the blind hole center line can be detected (4) and further the hole center position can be detected from the detection signal (5).

Since the fluorescence intensity on the hole center position and the hole center position are detected by executing the scanning twice, the residual resin level in a specific area on the center line can be inspected from the detection values (6). In the embodiment, as many fluorescence signals on the hole center line as the number of evaluation areas with the hole center position as the center are integrated and the residual resin level is detected. Even to inspect a blind hole where the residual resin on the center differs from that on the periphery, a shift between the laser application position and the blind hole position is detected and a specific position of the blind hole bottom is inspected, so that a high-reliability inspection with few variations can be accomplished.

Further, in the embodiment, if the evaluation area is made as large as the hole diameter, the vicinity of a hole wall face can be inspected, so that even a hole having a possibility for becoming defective because resin exists on the periphery although the vicinity of the hole center is at a good level, such as the hole made with the number of shots, five pulses, can be inspected reliably.

The above-described inspection, which can be carried out by twice scanning, is at very high speed. With our experimental apparatus, it turned out that 90 holes can be inspected per second.

If an inspection of a residual resin level with higher accuracy is required, the laser scanning and the residual resin detection in (4) to (6) in FIG. 3 may be executed two times or more and their outputs may be averaged. Generally, for random noise, it is known that the S/N ratio is improved in proportion to the square root of n by performing n repetitions.

Figure 4A:
FIGS. 4A and 4B are drawings to describe a method of detecting a hole position from a fluorescence signal.
Figure 4B:
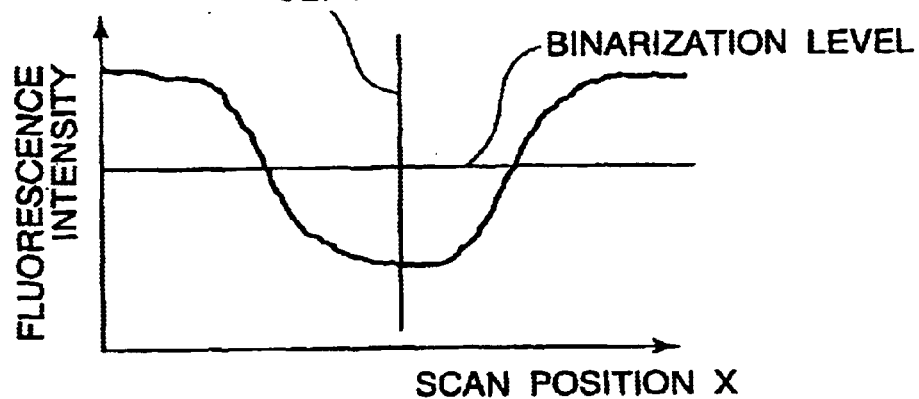

FIGS. 4A and 4B are drawings to describe an example of detecting the hole center position from the fluorescence signal in (3) and (5) above. Since the surface of a direct image board is covered with a thick resin and resin is lessened only on the bottom of a blind hole, the fluorescence signal when laser beam is scanned becomes a signal whose level is low on the hole bottom. If the signal is binarized and the center-of-gravity position of the lower-level one is calculated, the hole center position can be detected.

In the description of the embodiment, the galvanomirrors are taken as an example, but a similar advantage is also provided if AO (acoustooptic element), EO (electromagnetic optical element), etc., is used for scanning.

Second Embodiment

Figure 5:
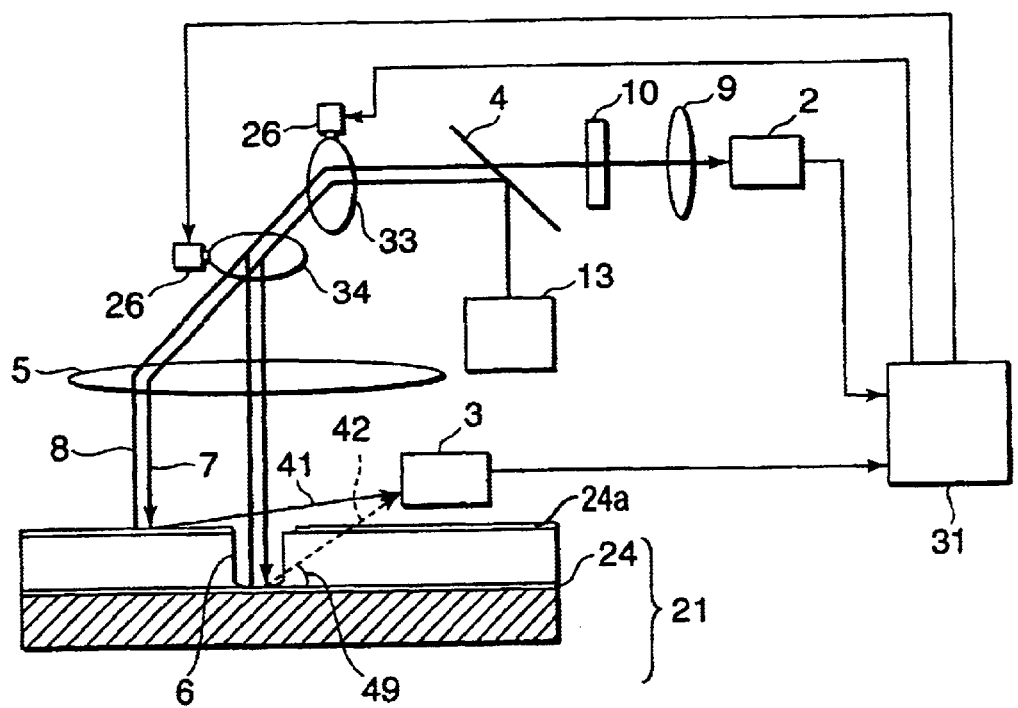
FIG. 5 is a drawing to show the configuration of a laser inspection apparatus of a second embodiment of the invention.

Since fluorescence is not generated on a conformal board because its surface is copper foil 24a, a blind hole cannot be detected. FIG. 5 is a drawing to show the configuration of a laser inspection apparatus of a second embodiment of the invention. It is a drawing to describe an optical system for discriminating surface copper foil 24a on a conformal board from copper foil 24 on the bottom of blind hole in the conformal board. The laser inspection apparatus of the embodiment is provided by attaching a photodetector 3 to the laser inspection apparatus in FIG. 1. The photodetector 3 is placed in a slanting direction relative to a blind hole. Copper foil contains fine asperities and upon application of laser beam 7, scattered reflected light is generated. Numeral 41 denotes reflected light scattered by irradiating laser beam to the copper foil 24a on the surface of a printed wiring board 21. Numeral 42 denotes reflected light scattered by irradiating laser beam to the bottom of the blind hole. The reflected light 41 on the copper foil 24a on the board surface is detected by the detector 3, but the reflected light 42 on the hole bottom is shielded on the hole wall face and is not detected by the detector 3. Therefore, whether the laser application position is the copper foil 24a on the board surface or the copper foil 24 on the hole bottom according to the detection signal level of the detector 3. Even if the laser application position and the blind hole position shift largely from each other for some reason, if the reflected light level is greater than a threshold value, it can be determined that the laser application position is not the hole bottom, so that an erroneous determination of a detective piece to be a good piece can be eliminated. If laser scanning is executed over the blind hole and the detection signal of the photodetector 3 for reflected light is binarized, the blind hole can be detected. Since the fluorescence intensity and the reflected light intensity can be detected at the same time, high-speed inspection can be accomplished.

Further, to detect a shift between the laser application position and the blind hole position and precisely irradiating the laser beam to the blind hole in the conformal board, the scan method previously described with reference to FIGS. 3 and 4 and may be executed. However, to detect the hole center position in FIGS. 4A and 4B, a reflected light signal is used in place of the fluorescence signal. Since the reflected light signal at the scanning time over the conformal hole is lowered in level on the hole bottom like the fluorescence signal at the scanning time over the direct hole, the hole position can be detected by the same method.

Further, if an attachment angle 49 of the photodetector 3 for reflected light is set equal to or less than atan (aspect ratio of blind hole), the reflected light 42 from the hole bottom is completely shielded on the hole wall face, so that the copper foil on the hole bottom can be discriminated from the copper foil on the board surface more reliably.

Further, if a plurality of the photodetectors 3 for reflected light are placed so as to surround the blind hole, the scan directional property of the detection signal is eliminated. This means that the copper foil on the hole bottom can be discriminated from the copper foil on the board surface reliably regardless of the scanning direction.

If an optical fiber is placed in the surroundings and reflected light condensed is detected by the detector 3, the detection system becomes simple and inexpensive.

Third Embodiment

Figure 6:
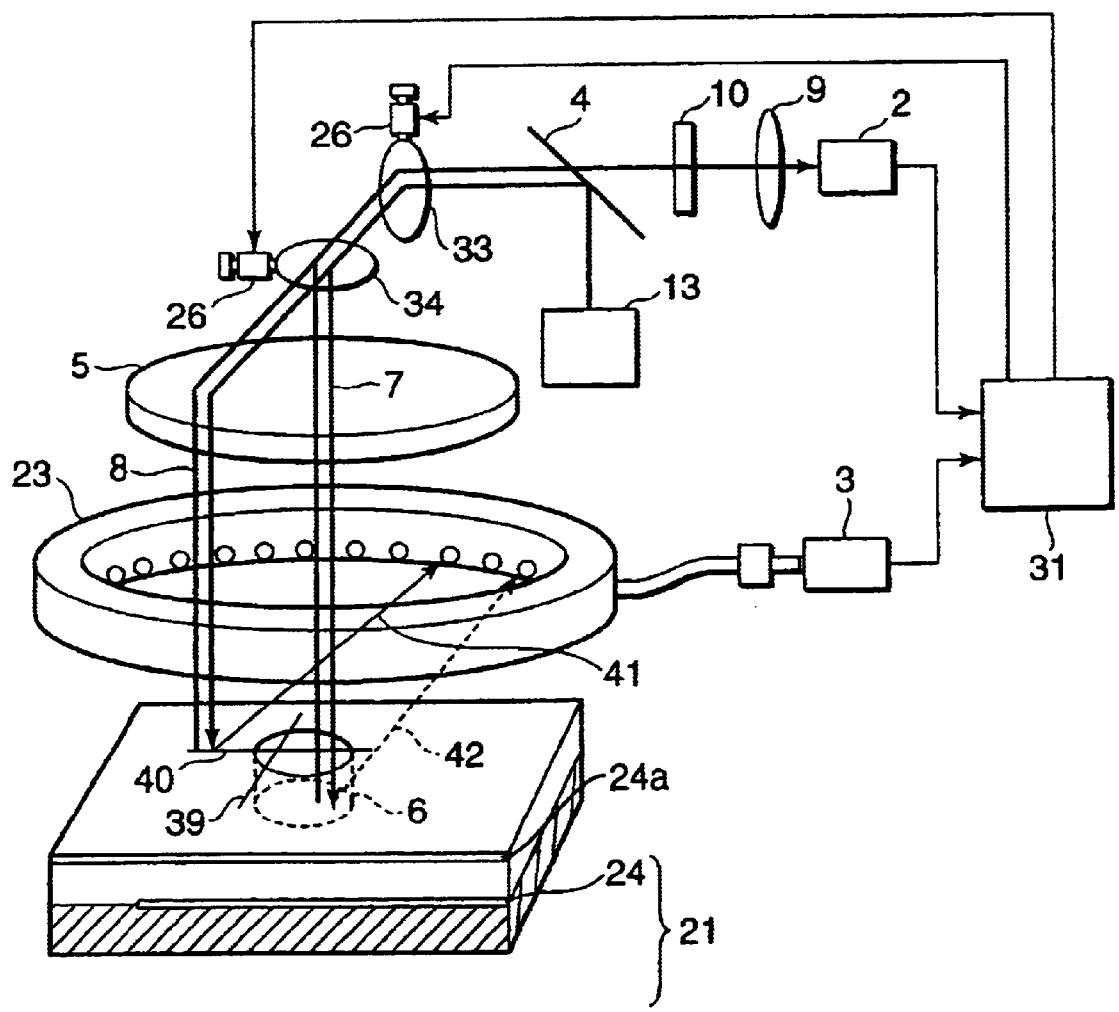
FIG. 6 is a drawing to show the configuration of a laser inspection apparatus of a third embodiment of the invention.

A laser inspection apparatus of a third embodiment of the invention in FIG. 6 has the same configuration as the laser inspection apparatus of the second embodiment previously described with reference to FIG. 5 except that a ring light guide 23 is used for condensing reflected light. The ring light guide 23 is developed essentially for illumination; it has a fiber arranged like a ring and an attachment angle 49 can be easily lessened and thus is fitted to the present application and the copper foil on the hole bottom can be discriminated from the copper foil on the board surface reliably.

Figure 7:
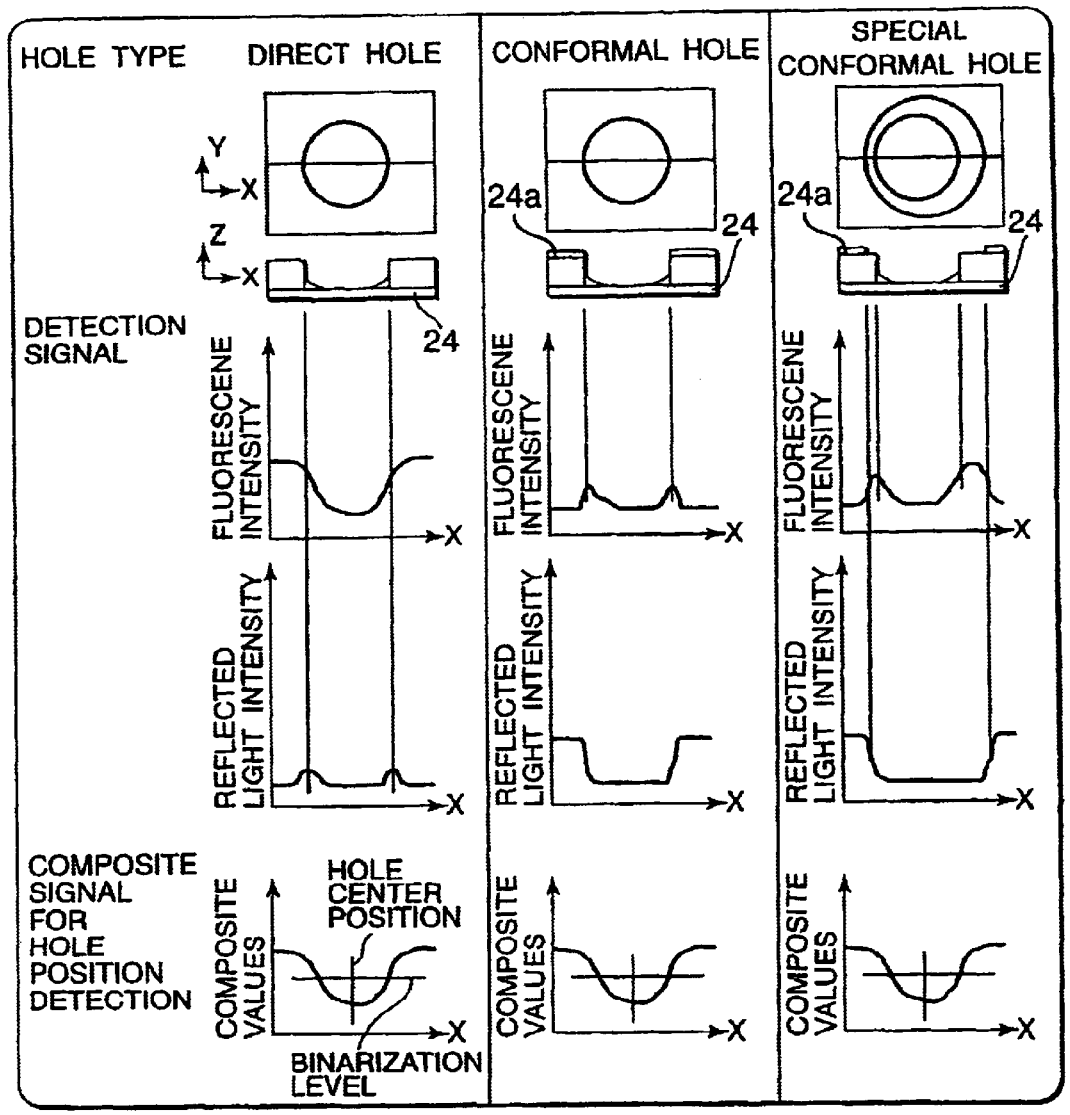
FIG. 7 is a drawing to describe a method of detecting a hole position from a fluorescence signal and a reflected light signal.

Blind holes include not only direct and conformal holes, but also a special blind hole machined in a smaller beam diameter than a diameter subjected to etching machining on copper foil of the board surface. The holes may be mixed in one printed wiring board. FIG. 7 is a drawing to describe a procedure for detecting a blind hole from a fluorescence signal and a reflected light signal in such a board. The fluorescence signal and the reflected light signal are lowered in level on the hole bottom regardless of the type of blind hole. If the board surface is resin, the fluorescence signal level becomes high; if the board surface is copper foil, the reflected light signal becomes high. Therefore, a composite (sum) signal of two detection signals is made lower in level on the hole bottom than that on the board surface regardless of the type of hole. Therefore, if the composite signal is binarized with one threshold value, the hole bottom can be detected.

Consequently, even on the printed wiring board in which direct and conformal holes are mixed, even if the laser application position and the blind hole position shift largely from each other for some reason, it can be determined that the laser application position is not the hole bottom, so that an erroneous determination of a defective piece to be a good piece can be eliminated. If laser scanning is executed over the blind hole and the composite signal is binarized and the center-of-gravity position of the lower-level one is calculated, the hole center position can be detected.

Further, in the embodiment, if the scanning previously described with reference to FIGS. 3 and 4 is executed, even on the printed wiring board in which direct and conformal holes are mixed, the center of the blind hole can be detected and it is made possible to conduct an inspection of precisely irradiating the laser beam to the blind hole. To detect the hole center position in FIGS. 4A and 4B, the composite signal may be used in place of the fluorescence signal.

Figure 8A:
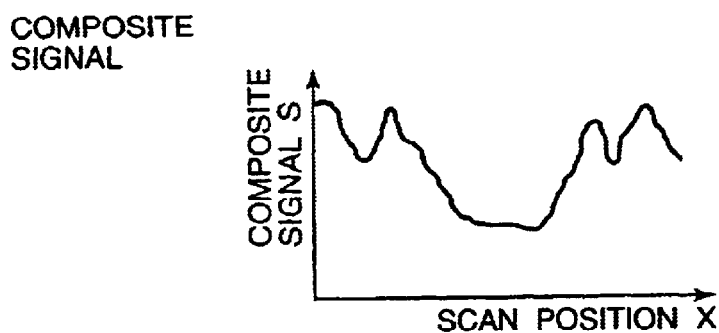
FIGS. 8A to 8C are drawings to describe a hole position detection procedure by discretization and sort processing.
Figure 8B:
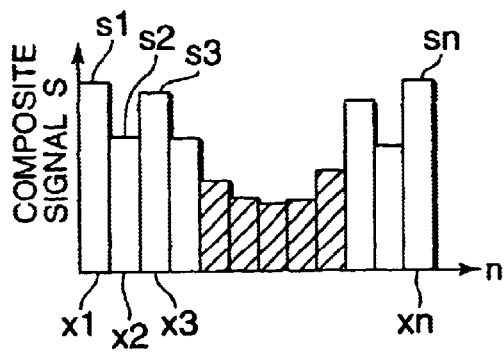
Figure 8C:
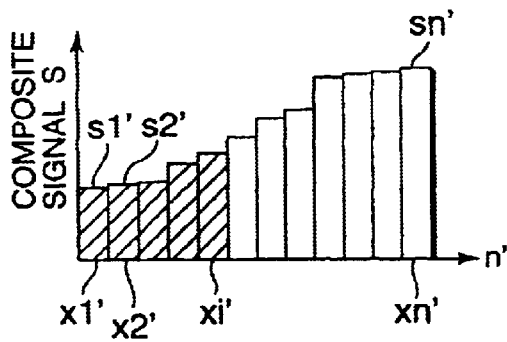
Figure 9:
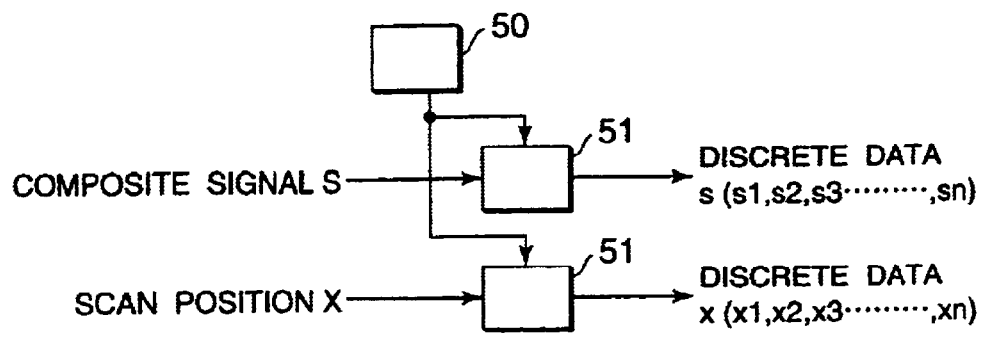
FIG. 9 is a drawing to describe a discretization circuit.

FIGS. 8 and 9 are drawings to describe another hole center position detection method in the embodiment. FIGS. 8A to 8C are drawings to describe a hole center position detection procedure by discretization and sort processing and FIG. 9 is a drawing to show one example of a discretization circuit. In FIG. 9, numeral 50 denotes a clock generator and numeral 51 denotes a latch circuit.

When laser beam is applied to the board surface, strong fluorescence or reflected light is detected and at the same time, a large noise component is also detected because of the effect of output variation of a laser or contents contained in resin. As compared with this, fluorescence or reflected light is little detected from copper foil on the hole bottom, thus the noise component is also small. Therefore, if a hole bottom detection signal is used, the hole center position can be detected reliably. Specifically, as shown in FIGS. 8A to 8C, first, while laser beam is scanned at equal speed, a detected composite signal and scan position signal are latched on the same clock for discretization. Next, the discretization data is sorted in the ascending order of the composite signal level. As many scan position data pieces as the number corresponding to the hole bottom diameter from the top are averaged and the hole center position is detected. In our experiment, if the detection signal contains much noise, it has been shown that the center position of each blind hole can be detected more reliably as compared with use of the binarization method. Of course, to inspect a board with direct holes only, the fluorescence signal may be used as the hole position detection signal in place of the composite signal.

Fourth Embodiment

Figure 10:
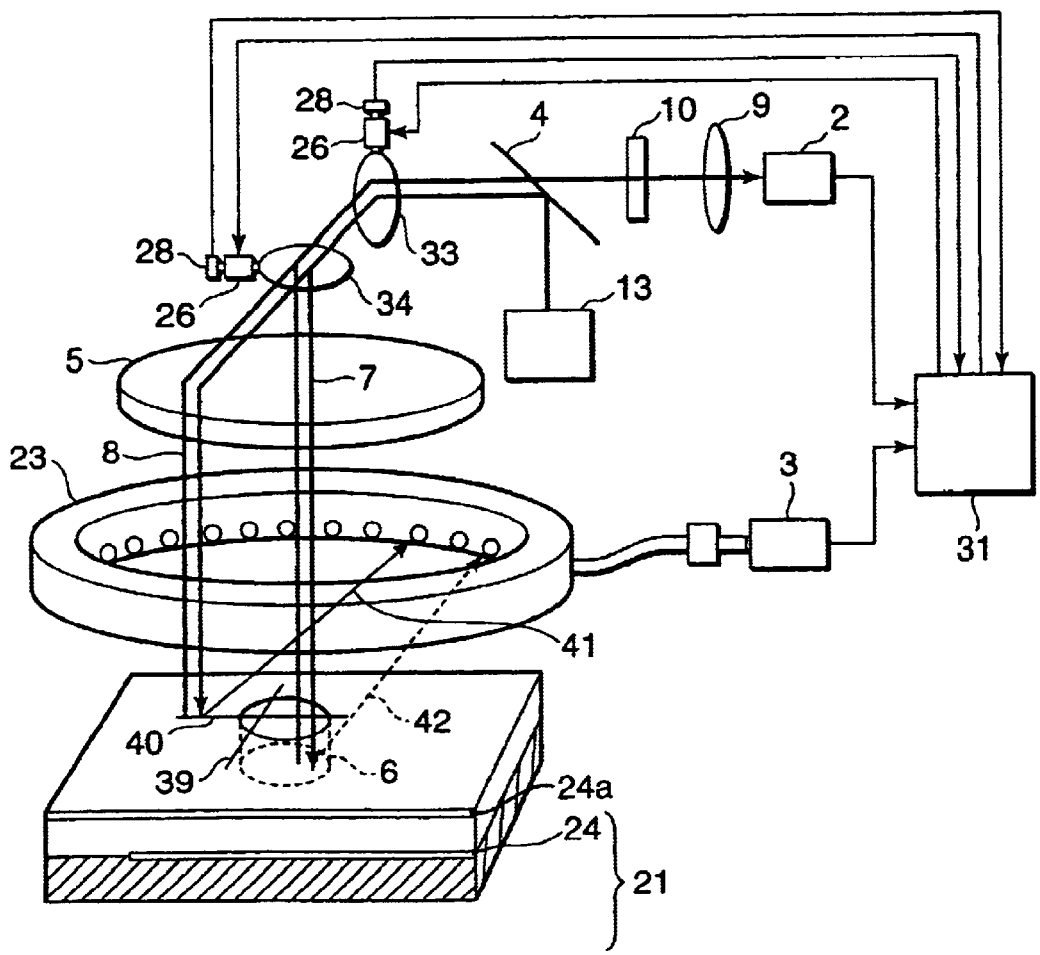
FIG. 10 is a drawing to show the configuration of a laser inspection apparatus of a fourth embodiment of the invention.
Figure 11:
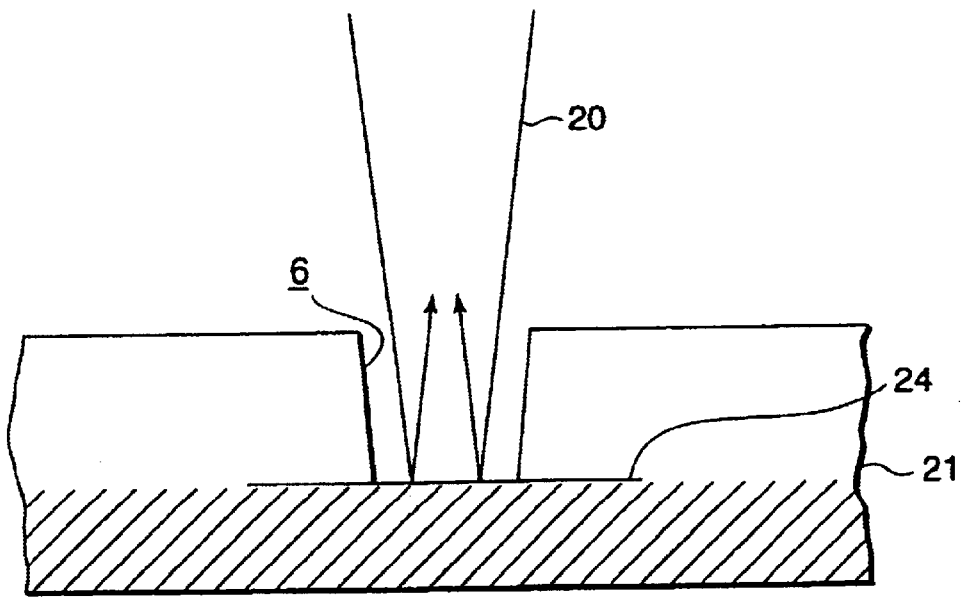
FIG. 11 is a schematic diagram to show laser machining of a printed wiring board.
Figure 12:
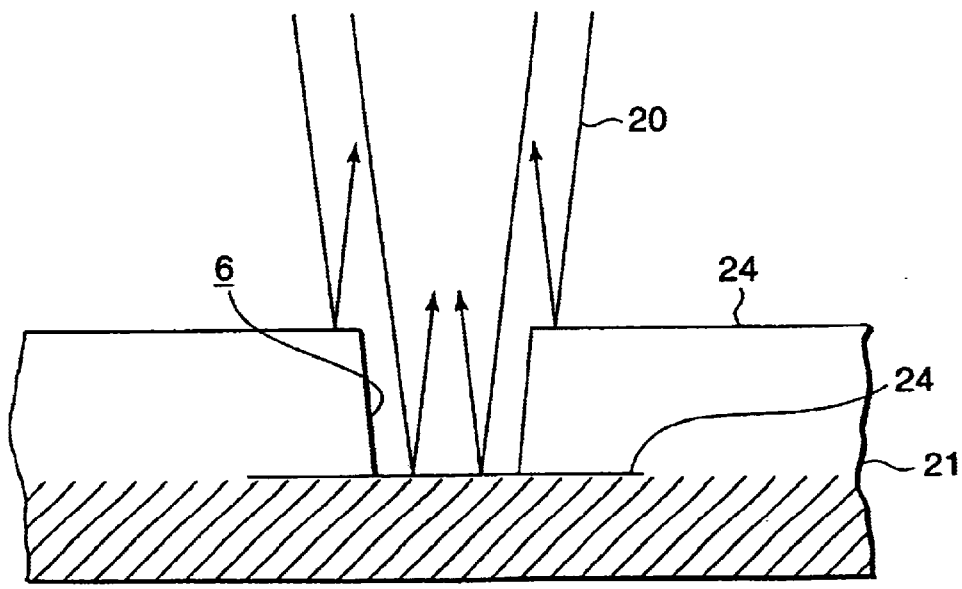
FIG. 12 is a schematic diagram to show laser machining of a printed wiring board.
Figures 13, 14:
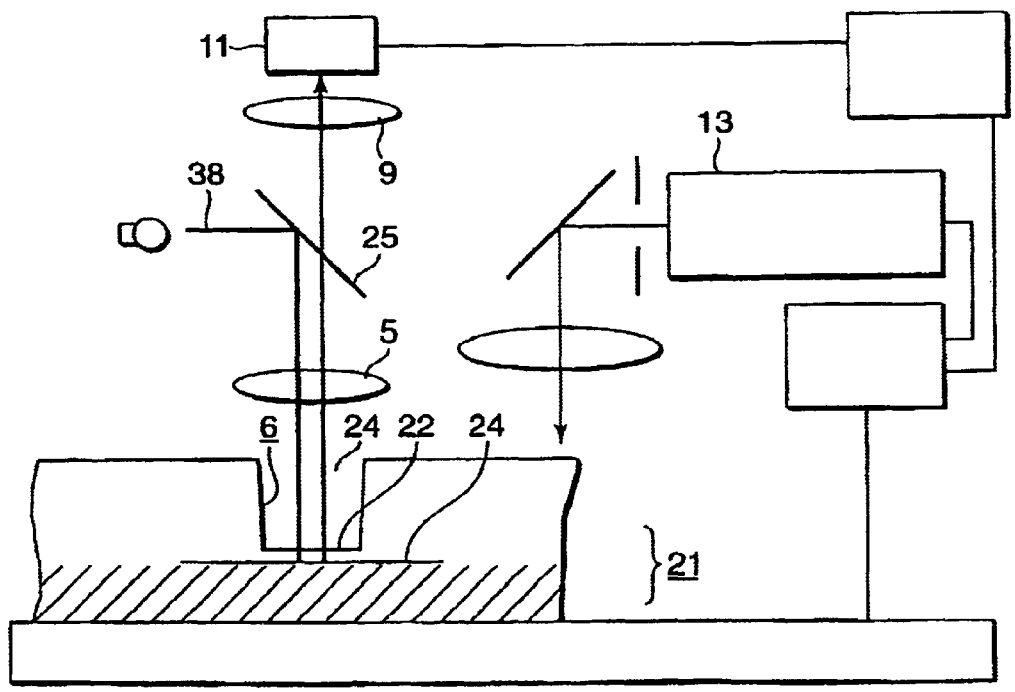
FIG. 13 is a schematic diagram to show distributions of remaining resin.
FIG. 14 is a schematic diagram to show an inspection apparatus in a related art.
Figure 15:
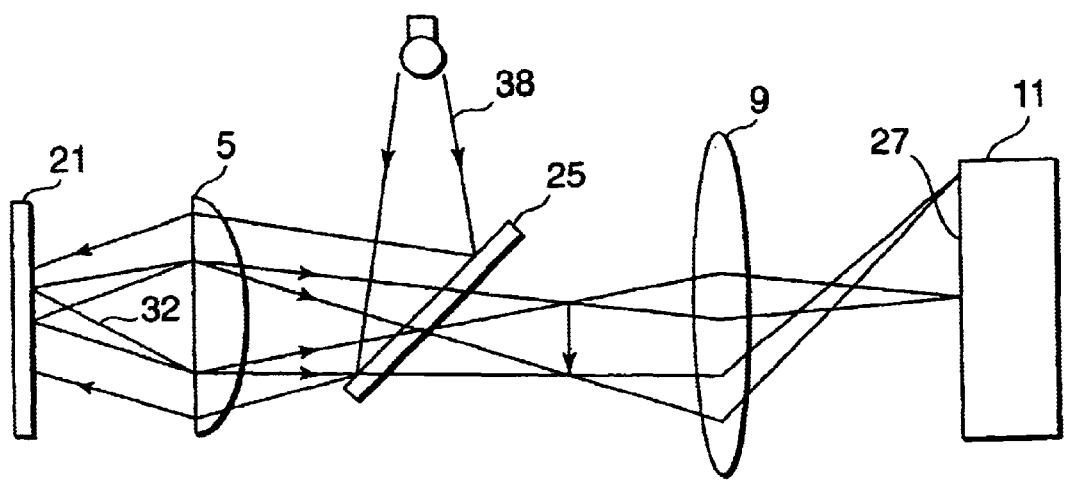
FIG. 15 is a schematic diagram to show the inspection apparatus in the related art.
Figure 16:
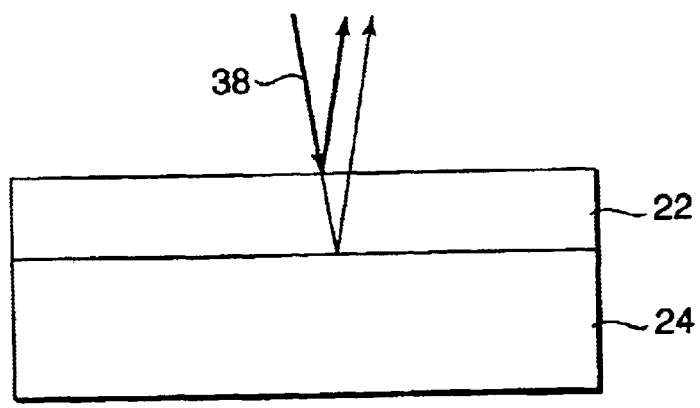
FIG. 16 is schematic drawing to show how white light is applied to a resin part.
Figure 17:
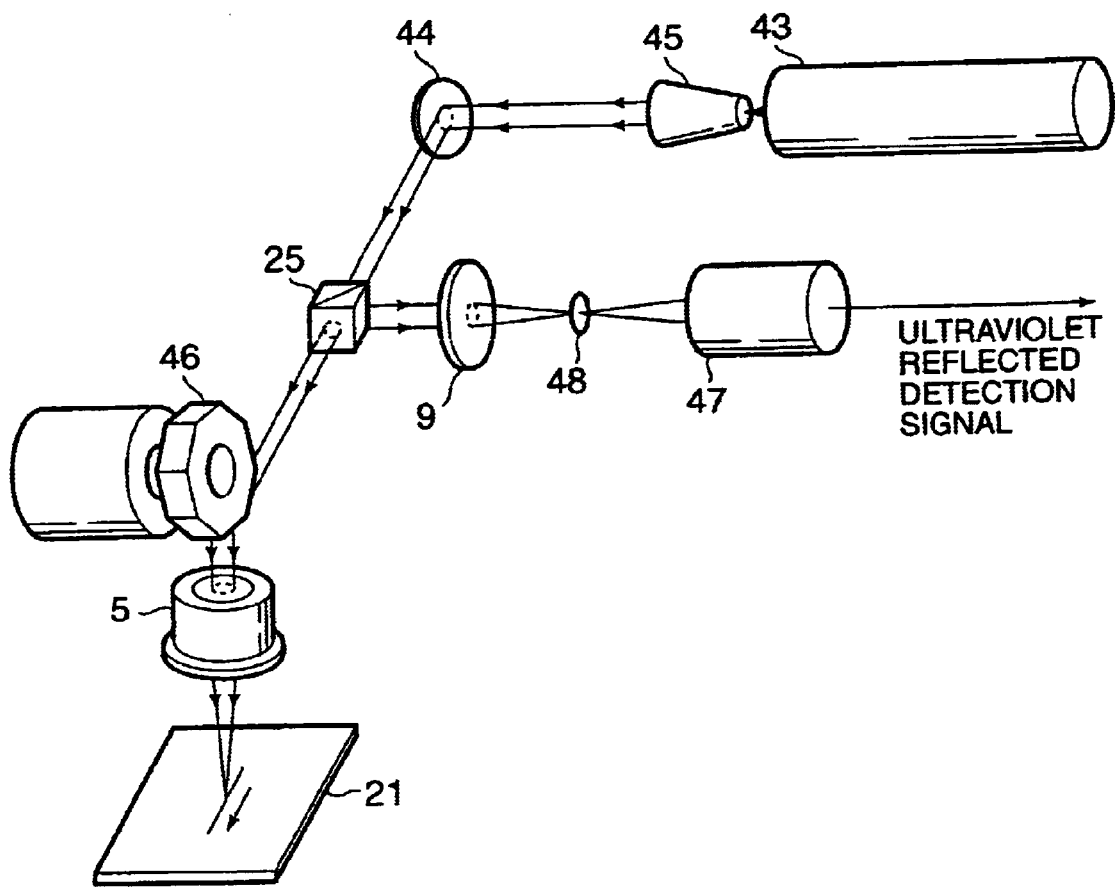
FIG. 17 is a schematic diagram to show an inspection apparatus in a related art.

FIG. 10 is a drawing to show the configuration of a laser inspection apparatus of a fourth embodiment of the invention. The laser inspection apparatus of the embodiment is a laser inspection apparatus wherein in the third embodiment, the scan position signal detected by position detectors 28 of galvanomirrors is input directly to a central control room 31; it can also be applied to the first and second embodiments, needless to say. For each galvanometer 26 for driving the galvanomirror, a servo system is configured to control the scan position. Generally, in the position servo system, a follow-up lag proportional to the scan speed occurs. Thus, particularly when the scan speed is high, the scan command position and the actual scan position shift from each other and the hole position detection accuracy worsens. In the fourth embodiment, the actual scan position is detected by the position detectors 28, so that it is made possible to detect the hole position with high accuracy with no shift if high-speed scanning is executed; a high-reliable residual resin inspection can be conducted at high speed.

The laser inspection apparatus according to one aspect of the invention comprises a light source for outputting laser beam, application means for irradiating the laser beam from the light source to any desired position of a detected body, first detection means for detecting fluorescence generated from the detected body to which the laser beam is applied, and second detection means for detecting reflected light scattered on a surface of the detected body to which the laser beam is applied. Thus, the laser inspection apparatus can use both the fluorescence intensity and the reflected light intensity to inspect the surface of the detected body, so that it can precisely detect the shape of the surface of the detected body. Since both the fluorescence intensity and the reflected light intensity can be detected at the same time by one laser scanning, inspection can be conducted at high speed.

The laser inspection apparatus according to another aspect of the invention comprises a light source for outputting laser beam, application means for irradiating the laser beam from the light source to any desired position on a board formed with a recess, detection means for detecting fluorescence generated from the board to which the laser beam is applied and outputting a detection signal, and control means for controlling the application means based on the detection signal, characterized in that the application means scans laser beam in a predetermined direction in the proximity of the recess, the detection means detects strength change of the fluorescence generated from the board as the laser beam is scanned, and outputs a detection signal, and the control means calculates a tentative center position of the recess on the scan line based on the detection signal, then the application means is controlled by the control means so as to scan laser beam in a direction passing through the calculated tentative center position and orthogonal to the scan line. Thus, reliable scanning can be executed over the line passing through the center of the recess and the recess can be inspected. Since the above-mentioned inspection can be accomplished by twice scanning and thus can be executed at high speed.

The control means discretizes the detection signal and sorts the discretized data in the level order of the detection signal and further makes a comparison with the diameter of the recess previously stored, thereby calculating the tentative center position of the recess. Thus, if the noise of the signal on the board surface is large, the center position of the recess is detected reliably and inspection is conducted on the center line of the recess, so that high-reliability inspection can be carried out.

The laser inspection apparatus according to still another aspect of the invention comprises a light source for outputting laser beam, application means for irradiating the laser beam from the light source to any desired position on a board formed with a recess, first detection means for detecting fluorescence generated from the board to which the laser beam is applied and outputting a first detection signal, second detection means for detecting reflected light scattered on a surface of the board to which the laser beam is applied and outputting a second detection signal, and control means for controlling the application means based on the first and second detection signals, characterized in that the application means scans laser beam in a predetermined direction in the proximity of the recess, the first detection means detects strength change of the fluorescence generated from the board as the laser beam is scanned, and outputs a first detection signal, the second detection means detects strength change of the reflected light scattered on the board as the laser beam is scanned, and outputs a second detection signal, and the control means calculates a tentative center position of the recess on the scan line based on the first and second detection signals, then the application means is controlled by the control means so as to scan laser beam in a direction passing through the calculated tentative center position and orthogonal to the scan line. Thus, if the material forming the board top surface is the same as the material forming the recess bottom, a signal for enabling them to be distinguished from each other can be provided and it is made possible to detect the recess. Thus, even if the laser application position and the recess position shift largely from each other for some reason, it can be determined that the laser application position is not the recess, so that an erroneous determination of a defective piece to be a good piece can be eliminated. Since both the fluorescence intensity and the reflected light intensity can be detected at the same time by one laser scanning, high-speed inspection can be accomplished.

The control means discretizes the first detection signal and sorts the discretized data in the level order of the first detection signal and further makes a comparison with the diameter of the recess previously stored, thereby calculating the tentative center position of the recess. Thus, if the noise of the signal on the board surface is large, the center position of the recess is detected reliably and inspection is conducted on the center line of the recess, so that high-reliability inspection can be carried out.

The control means discretizes the second detection signal and sorts the discretized data in the level order of the second detection signal and further makes a comparison with the diameter of the recess previously stored, thereby calculating the tentative center position of the recess. Thus, if the noise of the signal on the board surface is large, the center position of the recess is detected reliably and inspection is conducted on the center line of the recess, so that high-reliability inspection can be carried out.

The second detection means is placed so that the angle from the board face is set equal to or less than the aspect ratio of the recess. Thus, it is made possible to detect the recess more reliably and an erroneous determination caused by a shift between the laser application position and the recess position can be suppressed.

The second detection means is placed like a ring. Thus, it is made possible to detect the recess reliably regardless of the scanning direction and an erroneous determination caused by a shift between the laser application position and the recess position can be suppressed.

The control means combines the first and second detection signals. Thus, if the material forming the board top surface and the material forming the recess bottom are the same, different, or mixed, a composite signal for enabling the board top surface and the recess bottom to be distinguished from each other can be provided and it is made possible to detect the recess. an erroneous determination caused by a shift between the laser application position and the blind hole position can be suppressed.

The control means discretizes a composite signal provided by combining the first and second detection signals and sorts the discretized data in the level order of the composite signal and further makes a comparison with the diameter of the recess previously stored, thereby calculating the tentative center position of the recess. Thus, if the noise of the signal on the board surface is large, the center position of the recess is detected reliably and inspection is conducted on the center line of the recess, so that high-reliability inspection can be carried out.

The application means executes scanning in the same direction two times or more. Thus, a high-accuracy inspection with few variations can be accomplished.

The laser inspection apparatus further includes position detection means for detecting an actual scan position at the laser scanning time. Thus, worsening the recess position detection accuracy depending on the application position can be prevented and the scan speed can be increased.

What is claimed is:

1. A laser inspection apparatus comprising:

a light source for outputting laser light;

application means for applying the laser light output from the light source to any desired position on a board formed with a recess;

detection means for detecting fluorescence generated from the board to which the laser light is applied and outputting a detection signal; and control means for controlling the application means based on the detection signal, wherein the application means scans laser light a predetermined direction in the proximity of the recess, the detection means detects a strength change of the fluorescence generated from the board as the laser light is scanned, and outputs a detection signal, and the control means calculates a tentative center position of the recess on the scan line based on the detection signal, then the application means is controlled by the control means so as to scan laser light in a direction passing through the calculated tentative center position and orthogonal to the scan line.

2. The laser inspection apparatus as claimed in claim 1 wherein the control means discretizes the detection signal and sorts the discretized data in the level order of the detection signal and further makes a comparison with a predetermined numerical value, thereby calculating the tentative center position of the recess.

3. A laser inspection apparatus comprising:

a light source for outputting laser light;

application means for applying the laser light output from the light source to any desired position on a board formed with a recess;

first detection means for detecting fluorescence generated from the board to which the laser light is applied and outputting a first detection signal;

second detection means for detecting reflected light scattered on a surface of the board to which the laser light is applied and outputting a second detection signal; and control means for controlling the application means based on the first and second detection signals, wherein the application means scans laser light in a predetermined direction in the proximity of the recess, the first detection means detects a strength change of the fluorescence generated from the board as the laser lights is scanned, and outputs a first detection signal, the second detection means detects a strength change of the reflected light scattered on the board as the laser light is scanned, and outputs a second detection signal, and the control means calculates a tentative center position of the recess on the scan line based on the first and second detection signals, then the application means is controlled by the control means so as to scan laser light in a direction passing through the calculating tentative center position and orthogonal to the scan line.

4. The laser inspection apparatus as claimed in claim 3 wherein the control means discretizes the first detection signal and sorts the discretized data in the level order of the first detection signal and further makes a comparison with a predetermined numerical value, thereby calculating the tentative center position of the recess.

5. The laser inspection apparatus as claimed in claim 3 wherein the control means discretizes the second detection signal and sorts the discretizes data in the level order of the second detection signal and further makes a comparison with a predetermined numerical value, thereby calculating the tentative center position of the recess.

6. The laser inspection apparatus as claimed in claim 3 wherein the second detection means is placed so that an angle from the board face is set equal to or less than an aspect ratio of the recess.

7. The laser inspection apparatus as claimed in claim 3 wherein the second detection means is placed like a ring.

8. The laser inspection apparatus as claimed in claim 3 wherein the control means combines the first and second detection signals.

9. The laser inspection apparatus as claimed in claim 8 wherein the control means discretizes a composite signal provided by combining the first and second detection signals and sorts the discretized data in the level order of the composite signal and further makes a comparison with a predetermined numerical value, thereby calculating the tentative center position of the recess.

10. The laser inspection apparatus as claimed in claim 1 wherein the application means executes scanning in the same direction two times or more.

11. A laser inspection apparatus for inspecting a detected body previously formed with at least one recess comprising:
    a light source which outputs a laser beam;
    a scanning optical system which irradiates the laser beam from the light source to any desired position of the detected body;
    a detector which detects fluorescence generated from the recess to which the laser beam is applied and outputs a detection signal; and
    a processing unit which controls the scanning optical system based on the detection signal,
        wherein the scanning optical system scans the laser beam in a predetermined direction in the proximity of the recess, the detector detects a strength change of the fluorescence generated from the recess as the laser beam is scanned and outputs the detection signal, and the processing unit calculates a tentative center position of the recess on the scan line based on the detection signal, and wherein the scan optical system is subsequently controlled by the processing unit so as to scan the laser beam in a direction passing through the calculated tentative center position and orthogonal to said scan line.

12. A laser inspection apparatus for inspecting a detected body previously formed with at least one recess comprising:
    a light source which outputs a laser beam;
    a scanning optical system which irradiates the laser beam from the light source to any desired position on a detected body;
    a first detector which detects fluorescence generated from the recess to which the laser beam is applied and outputs a first detection signal;
    a second detector which detects reflected light scattered on a top surface of the detected body to which the laser beam is applied and outputs a second detection signal; and
    a processing unit which controls the scanning optical system based on the first and second signals,
        wherein the scanning optical system scans the laser beam in a predetermined direction in the proximity of the recess, the first detector detects a strength change of the fluorescence generated from recess as the laser beam is scanned and outputs the first detection signal, the second detector detects a strength change of the reflected light scattered on the top surface of the detected body as the laser beam is scanned and outputs the second detection signal, and the processing unit calculates a tentative center position of the recess on the scan line based on the first and second detection signals, and wherein the scan optical system is subsequently controlled by the processing unit so as to scan the laser beam in a direction passing the through the calculated tentative center position and orthogonal to said scan line.

* * * * *